(12) United States Patent
Mescheder et al.

(10) Patent No.: US 9,233,094 B2
(45) Date of Patent: Jan. 12, 2016

(54) METHOD OF ADMINISTERING A CATIONIC LIPOSOMAL PREPARATION

(75) Inventors: Axel Mescheder, Worthsee (DE); Matthias Karrasch, Erlangen (DE)

(73) Assignee: Medigene AG, Planegg-Martinsried (DE)

( * ) Notice: Subject to any disclaimer, the term of this patent is extended or adjusted under 35 U.S.C. 154(b) by 900 days.

(21) Appl. No.: 11/919,700

(22) PCT Filed: May 4, 2006

(86) PCT No.: PCT/EP2006/004185
§ 371 (c)(1),
(2), (4) Date: Oct. 31, 2007

(87) PCT Pub. No.: WO2006/117220
PCT Pub. Date: Nov. 9, 2006

(65) Prior Publication Data
US 2009/0047337 A1 Feb. 19, 2009

(30) Foreign Application Priority Data
May 4, 2005 (EP) .................................. 05 009 847

(51) Int. Cl.
*A61K 9/127* (2006.01)
*A61K 31/337* (2006.01)
*A61K 9/00* (2006.01)
*A61K 31/7068* (2006.01)
*A61K 45/06* (2006.01)

(52) U.S. Cl.
CPC ............. *A61K 31/337* (2013.01); *A61K 9/0019* (2013.01); *A61K 9/1272* (2013.01); *A61K 31/7068* (2013.01); *A61K 45/06* (2013.01)

(58) Field of Classification Search
USPC .......................................................... 424/450
See application file for complete search history.

(56) References Cited

U.S. PATENT DOCUMENTS

| | | | |
|---|---|---|---|
| 5,621,001 A * | 4/1997 | Canetta et al. ................. 514/449 |
| 6,846,816 B2 * | 1/2005 | Borisy et al. ................ 514/225.8 |
| 7,112,338 B2 * | 9/2006 | McDonald et al. ............ 424/450 |
| 7,563,570 B2 * | 7/2009 | Costa et al. ................... 435/6.14 |
| 2002/0041888 A1 | 4/2002 | Flashner-Barak |
| 2003/0008014 A1* | 1/2003 | Shelness ....................... 424/499 |
| 2003/0087954 A1 * | 5/2003 | Palepu et al. ................. 514/449 |
| 2004/0076582 A1 * | 4/2004 | Dimatteo et al. ............ 424/1.49 |
| 2004/0241094 A1 | 12/2004 | Chung et al. |
| 2008/0063699 A1* | 3/2008 | Teifel et al. ................... 424/450 |

FOREIGN PATENT DOCUMENTS

| JP | 2004-507451 A | 3/2004 |
| JP | 2005-504070 A | 2/2005 |

(Continued)

OTHER PUBLICATIONS

Strieth et al. "Neovascular targeting chemotherapy: encapsulation of paclitaxel in cationic liposomes impairs functional tumor neovasculature." International Journal of Cancer 110: 117-124, 2004.

(Continued)

*Primary Examiner* — Gollamudi Kishore
(74) *Attorney, Agent, or Firm* — Lee & Hayes, PLLC

(57) ABSTRACT

The present invention relates to the use of pharmaceutical preparations comprising paclitaxel for administration to a human patient in need thereof.

29 Claims, 2 Drawing Sheets

(56) References Cited

FOREIGN PATENT DOCUMENTS

Figure 1:
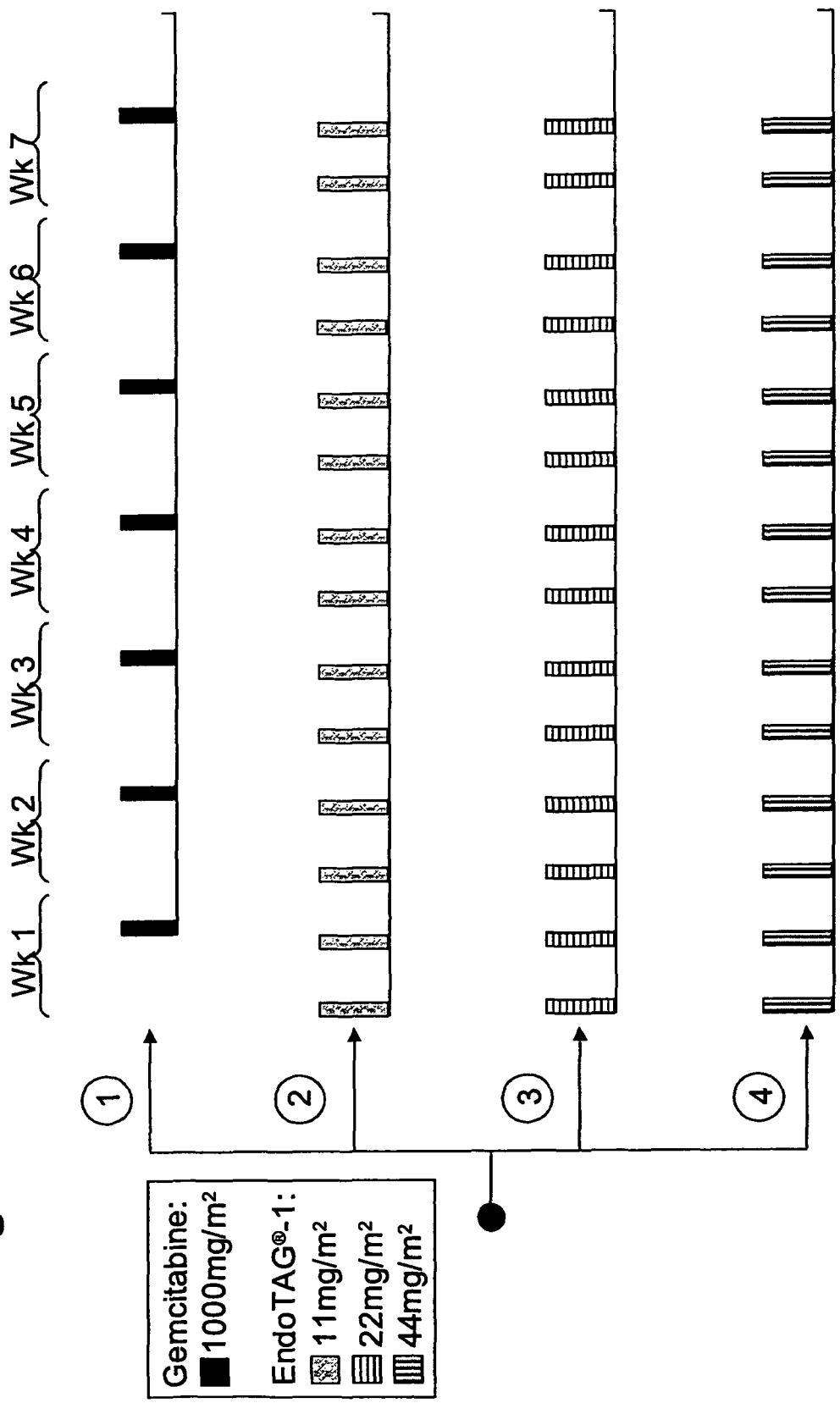

| WO | WO 01/17508 | 3/2001 |
|----|----|----|
| WO | 02/067928 A2 | 9/2002 |
| WO | WO 2005/039533 | 5/2005 |

OTHER PUBLICATIONS

Campbell et al. "Influence of cationic lipids on the stability and membrane properties of paclitaxel-containing liposomes." Journal of Pharmaceutical Sciences 90: 1091-1105, 2001.
Soepenberg et al. "Real-time pharmacokinetics guiding clinical decisions- phase I study of a weekly schedule of liposome encapsulated paclitaxel in patients with solid tumors." European Journal of Cancer 40: 681-688, 2004.
Fetterly et al. "Pharmcokinetics of paclitaxel-containing liposomes in rats." AAPS PharmSci 5: E32, 1-12, 2003.
Löhr et al., "Cationic liposomal paclitaxel plus gemcitabine or gemcitabine alone in patients with advanced pancreatic cancer: a randomized controlled phase II trial," Annals of Oncology, 2011, doi:10.1093/annonc/mdr379.
MediGene, "MediGene reports additional phase II results of EndoTAGÔTM-1 for the treatment of triple receptor-negative breast cancer," MediGene Press Release, 2010, p. 1-3.
Schmitt-Sody et al, "Neovascular Targeting Therapy: Paclitaxel Encapsulated in Cationic Liposomes Improves Antitumoral Efficacy", Clinical Cancer Research, vol. 9, pp. 2335-2341, Jun. 2003.
Kuntsfeld et al, "Paclitaxel Encapsulated in Cationic Liposomes Diminishes Tumor Angiogenesis and Melanoma Growth in a "Humanized" SCID Mouse Model", The Journal of Investigative Dermatology, vol. 120, pp. 479-482, Mar. 2003.
Reagan-Shaw et al, "Dose translation from animal to human studies revisited", FASEB Journal, pp. 1-3, Oct. 2007.
Awada et al., "P3-17-06: Final results of a controlled, randomized 3-arm phase II trial of EndoTAG®-1, a cationic liposomal formulation of paclitaxel targeting tumor endothelial cells, in advanced triple-negative breast cancer (TNBC)," Cancer Research, 2011, vol. 71.
Cardenes et al., "Locally Advanced Pancreatic Cancer: Current Therapeutic Approach," The Oncologist, 2006, pp. 612-623, vol. 11.
Constantinou et al., "Paclitaxel and Concurrent Radiation in Upper Gastrointestinal Cancers," Cancer Investigation, 2003, pp. 887-896, vol. 21, No. 6.
Deutsches Krebsforschungszentrum Krebsinformationsdienst, "Krebsforschung: So laufen vorklinische klinische Studien ab," DKFZ, Accessed: Aug. 18, 2010, Found at: http://www.krebsinformationsdienst.de/grundlagen/neue-verfahren-klinische-forschung.php (machine translation included).
Löhr et al., "Cationic liposomal paclitaxel plus gemcitabine or gemcitabine alone in patients with advanced pancreatic cancer: a randomized controlled phase II trial," Annals of Oncology, 2011, doi:10.1093/annonclmdr379.
MediGene, "MediGene reports additional phase II results of EndoTAG^TM-1 for the treatment of triple receptor-negative breast cancer," MediGene Press Release, 2010, p. 1-3.
Moulder et al., "Applicability of Animal Tumor Data to Cancer Therapy in Humans," Int. J. Radiation Oncology Biol. Phys., 1988, pp. 913-927, vol. 14.
Oettle et al., "Paclitaxel as weekly second-line therapy in patients with advanced pancreatic carcinoma," Anticancer Drugs, 2000, pp. 635-638, vol. 11.
Perez et al., "Efficacy of ixabepilone in ER/PR/HER2-negative (triple-negative) breast cancer," Breast Cancer Res. Treat, 2010, pp. 261-271, vol. 121.
Sledge et al., Phase III Trial of Doxorubicin, Paclitaxel, and the Combination of Doxorubicin and Paclitaxel as Front-Line Chemotherapy for Metastic Breast Cancer: an Intergroup Trial (E1193), Journal of Clinical Oncology, 2003, pp. 588-592, vol. 21, No. 4.

* cited by examiner

METHOD OF ADMINISTERING A CATIONIC LIPOSOMAL PREPARATION

RELATED APPLICATIONS

The present application is a U.S. National Phase Application of International Application No. PCT/EP2006/004185, filed May 4, 2006, which claims the benefit of European Patent Application No. 05 009 847.4 filed May 4, 2005, both of which are herein incorporated by reference in their entirety.

Description

The present invention relates to the use of pharmaceutical preparations comprising paclitaxel for administration to a human patient in need thereof.

The use of antimitotic drugs, such as taxanes, as therapeutic agents for human patients suffering from diseases which are connected with enhanced mitosis are well known in the art.

Paclitaxel has a unique mechanism of action and a broad spectrum of antiproliferative activity because paclitaxel binds to microtubules and promotes tubulin polymerisation and stabilizes the assembled microtubules. As a result, paclitaxel blocks the cell cycle at prophase resulting in an accumulation of cells in the G2/M phase.

Unfortunately, paclitaxel has extreme low solubility in water, which makes it difficult to provide a suitable dosage form. Currently, paclitaxel is formulated and administered in a vehicle containing Cremophor EL (a polyethoxylated castor oil) and ethanol in a 50:50 (vol/vol) ratio. This solution is diluted 1:10 in saline before being administered to humans. However, various severe side reactions, such as hypersensitivity and hypertensive reactions, nephrotoxicity and neurotoxicity, for example, have been reported in patients due to Cremophor EL formulation.

Further, even though paclitaxel (among other antitumor drugs) is a potent, well-established standard antitumor drug ({Rowinsky, 1995 #1}, {Awada, 2002 #2}, {Seidman, 2003 #3}, {Romanini, 2003 #4}), drug-unresponsive tumors and metastases are observed frequently in cancer patients ({Blom, 1996 #5}, {Modi, 2002 #6}, {Ozols, 2003 #7}). Genetically instable, rapidly dividing tumor cells gain the capacity to overcome the growth inhibitory effect of a selected anti-cancer drug ({Vogelstein, 1988 #8}, {Kerbel, 1991 #9}). This capacity is usually not limited to a single drug (first line treatment) but extends to other drugs which are used after development of the first resistance. Hence, this phenomenon is called multi drug resistance (MDR).

As the number of available and approved anti-neoplastic drugs is very limited for many cancer types, many patients succumb since their cancer tissues express MDR-related genes. The obvious problem, therefore, is to find methods and means to kill drug-resistant tumors, especially drug resistant cells, which are already resistant against the respective drug.

A number of approaches were taken to deal with the above mentioned problems. The conventional strategy is to increase doses up to the maximal tolerated dose (MTD) and attempt to eradicate all tumor cells as quickly and completely as possible ({Schünemann, 1999 #10}, {Heidemann, 1997 #11}). It is obvious that this strategy causes severe side effects and can not be extended to longer periods. Therefore, this treatment schedule consists of cycles of one short treatment period (usually 1 day-1 week) at MTD and a treatment-free interval of several weeks (usually 3-4 weeks), to allow the patient to recover from the obligatory side effects ({Schünemann, 1999 #10}, {Heidemann, 1997 #11}, {Romanini, 2003 #4}).

In many instances, tumor growth can also restart during these drug-free periods. Most importantly, this approach fails in many patients where tumor cells develop a high level of resistance which enables them to accommodate with drug concentrations at the MTD. The patients become therapy refractory.

The most common solution is to start treatment with a second drug (second line treatment) ({Blom, 1996 #5}, {Awada, 2002 #2}, {Seidman, 2003 #3}, {Heinemann, 2003 #12}, {Thigpen, 2003 #13}). In the best case, the second line treatment is successful and tumor response is documented. A common experience however is that tumors only respond for a certain time leading to a temporary regression of the tumor. After that, tumors become also resistant to the second drug. It is possible to start treatment with a third drug (third line treatment). However, tumors may become also resistant to the third drug. Continuing with this strategy leads to development of multi drug resistant tumors which are finally refractory to all available anti-cancer drugs ({Blom, 1996 #5}, {Seidman, 2003 #3}, {Thigpen, 2003 #13}).

Another possibility is to treat patients immediately with a combination of 2 or more drugs ({Heinemann, 2003 #12}, {Kuenen, 2002 #14}, {Sledge, 2003 #15}, {Ozols, 2003 #7}, {Reck, 2003 #17}, {Romanini, 2003 #4}). This strategy can be more successful as it decreases the likelihood for development of a double drug resistance. However, this strategy needs to explore time and cost intensively suitable drug combinations. A second disadvantage is that the side effects may also increase ({Kuenen, 2002 #14}, {Ozols, 2003 #7}). The therapeutic window concomitantly becomes small and the toxic effects may overlay the envisioned therapeutic benefit. Also in this case, multi drug resistance may develop and the therapy becomes ineffective ({Zimpfer-Rechner, 2003 #18}, {Sledge, 2003 #15}, {Sledge, 2003 #16}, {Ozols, 2003 #7}).

The consequence of the negative experiences with such traditional treatment strategies is to develop more and more new drugs to extend the above described treatment options. Obviously, it is a very time and cost intensive race for more potent drugs which will eventually lead in many cases to therapy refractory tumors. In recent years, this recognition has led to a new approach to circumvent tumor resistance. It is based on the assumption that the MDR is caused by overexpression of enzymes which enable cells to expel chemotherapeutic drugs. The most famous member of this category of enzymes is called p-glycoprotein (p-gp). It is located in the cytoplasmic membrane and exports in an ATP-driven way ({Nobmann, 2001 #19}, {Thomas, 2003 #20}) compounds like paclitaxel or doxorubicin ({Harker, 1985 #21}, {Fellner, 2002 #22}, {Kiesewetter, 2003 #23}). This notion led to the development of p-gp inhibitors which are meant to reverse p-gp mediated drug resistance. Hence the term chemosensitizers was coined for this class of molecules. One of the first examples tested was verapamil. Clinical studies, however, revealed unsatisfactory results, possibly due to low specific activity ({Thomas, 2003 #20}, {Kohler, 2003 #24}). The further research led to a second generation of compounds which again were found not to be clinically applicable ({Leonard, 2002 #25}, {Thomas, 2003 #20}). Today a few substances of the third generation, one known as tariquidar, are in clinical trials ({Agrawal, 2003 #26}, {Callies, 2003 #27}). The usefulness and broad applicability of these compounds is, however, still unclear ({Leonard, 2002 #25}, {Thomas, 2003 #20}). Even though much improved in comparison to first generation chemosensitizers, third generation compounds also cause side effects and may have unforeseen consequences for the whole body. Extensive clinical testing is needed and it is so far uncertain if such approaches can become general practice in the future ({Leonard, 2002 #25}, {Thomas, 2003 #20}).

Different delivery systems have been used to enhance the effect of paclitaxel and/or reduce toxicity. Liposomes are one of many carriers that have been developed to enhance aqueous solubility and thus efficiency, combined with less toxicity.

U.S. Pat. No. 5,648,090, U.S. Pat. No. 5,424,073 and U.S. Pat. No. 6,146,659 (Rahman et al.) provide a liposomal encapsulated paclitaxel for a method for treating cancer in mammals. These patents disclose a method of administering to the host a pharmaceutical composition of a therapeutically effective amount of liposomes which include a liposome forming material, cardiolipin, and an agent such as paclitaxel, or an antineoplastic derivative of paclitaxel, or a mixture thereof, with a pharmaceutically acceptable excipient. In U.S. Pat. No. 6,146,659, a method of administering a taxane to a patient is provided by administering taxane over a period of less than an hour in an amount from about 75 to 300 mg/m$^2$, wherein the taxane is liposomally encapsulated. The liposomes disclosed therein are negatively charged.

Since the disclosure of McDonald et al., U.S. Pat. No. 5,837,283, it is known that positively charged liposomes specifically target angiogenic endothelial cells.

Strieth et al., 2004, Int. J. Cancer 110, 117-124 describe experiments in Syrian Golden hamsters using paclitaxel in cationic liposomes. The animals were treated with liposomal paclitaxel in a dose schedule three times a week.

The problem underlying the present invention was to provide an improved method of administering paclitaxel to a subject in need thereof in a therapeutically effective amount without severe side effects. The treatment schedule should minimize the time spent in clinical treatment for infusions while maintaining optimal treatment results.

The solution to the above problem is achieved by providing the embodiments characterized in the claims.

A first aspect relates to the use of a cationic liposomal preparation comprising at least one cationic lipid from about 30 mole % to about 99.9 mole %, paclitaxel in an amount of at least about 0.1 mole % and at least one neutral and/or anionic lipid from about 0 mole % to about 70 mole % for the manufacture of a pharmaceutical composition for administration
  (i) once in a week,
  (ii) twice in a week or
  (iii) a combination of (i) and (ii),
  wherein the monthly dose is about 0.1 mg/kg bw to about 20 mg/kg bw.

The combination (iii) of a once weekly administration (i) and a twice weekly administration (ii) is a weekly or biweekly alternating schedule.

Surprisingly, it was found in contrast to postulated anti-angiogenic neovascular targeting schedules, which favour daily dosing or multiple weekly dosing (Strieth et al. 2004, Int. J. Cancer 110, 117-124), that cationic liposomal preparations comprising a taxane, particularly paclitaxel are even more efficient in treating cancer even in a weekly or biweekly dosing schedule.

It was unexpectedly found that a continuous application of cationic liposomal paclitaxel once or twice a week at a low dose over a longer period of time, such as e.g. for several weeks, preferably at least seven weeks, is equally or even more effective than frequent applications of 3-5 times a week at a low dose over a shorter time period, e.g. of about four weeks interrupted by pause intervals of a week or several days.

Furthermore, it was unexpectedly found that a continuous application of cationic liposomal paclitaxel once or twice a week at a low dose over a longer period of time, e.g. of about several weeks or months, preferably of at least about seven weeks, is equally or even more effective than a once a week high dose application interrupted by pause intervals over a shorter period of time, e.g. of about four weeks.

Liposomal preparations comprising paclitaxel as disclosed herein can be used in combination therapy with a further active agent. A twice weekly application schedule was found to be especially suitable in combination therapy with a further active agent, particularly with gemcitabine.

Furthermore, the twice weekly schedule was found to be particularly suitable for combination therapy of liposomal paclitaxel, especially cationic liposomal paclitaxel (EndoTAG-1) in combination with gemcitabine in the treatment of pancreatic cancer, adenocarcinoma of the pancreas.

General advantages of the administration of liposomal paclitaxel are:
  high amounts of the active ingredient
  selective targeting
  improved efficacy
  lower side effects compared to traditional chemotherapy or to a preparation of neutral or anionic liposomes
  reduction of disease related pain
  improvement of quality of life
  stabilization of body weight during treatment
  synergistic effects with traditional therapy regimes Particular advantages of an once or twice weekly dosing schedule are as follows:
  less physical burden for the patient due to longer recovery times
  fewer hospitalization events
  the administration over a longer time frame of several weeks or months, preferably of at least seven weeks, is equally or even more efficacious than frequent applications over a shorter period of time The advantages of the once or twice weekly dosing schedule result in an improved quality of life for the patient.

The present pharmaceutical composition can be administered at a monthly dose of about 0.25 mg up to about 100 mg, particularly up to about 60 mg of liposomal paclitaxel/kg body weight (bw) of a patient, preferably of about 0.5 mg up to about 30 mg of liposomal paclitaxel/kg bw and more preferably of about 1.0 mg up to about 15 mg of liposomal paclitaxel/kg bw.

In a preferred embodiment the monthly dose ranges from between about 1 mg/kg bw to about 15 mg/kg, or about 0.5 mg/kg bw to about 7.5 mg/kg bw, about 2.2 mg/kg bw to about 12.3 mg/kg bw, about 1.1 to about 6.2 mg/kg bw, about 2.2 mg/kg bw to about 9 mg/kg bw, about 1.1 mg/kg bw to about 4.5 mg/kg bw, about 4.5 mg/kg bw to about 12.5 mg/kg bw or most preferably about 2.3 mg/kg bw to about 6.3 mg/kg bw.

A single unit dose ranges from between about 0.01 mg/kg bw to about 100 mg/kg bw, preferably between about 0.2 mg/kg bw to about 60 mg/kg bw, or is more preferably about 0.28 mg/kg bw, about 1 13 mg/kg bw or most preferably about 1.88 mg/kg bw.

In a preferred embodiment of the present invention the pharmaceutical composition is administered at a single unit dose ranging from about 0.01 to about 10 mg/kg bw, particularly about 0.05 to about 5 mg liposomal paclitaxel per kg of body weight. Preferably, a single dose is about 0.1 mg/kg bw to about 2.5 mg/kg bw, about 0.05 mg/kg bw to about 1.25 mg/kg bw, about 0.25 mg/kg bw to about 1.54 mg/kg bw, about 0.14 mg/kg bw to about 0.75 mg/kg bw, about 0.56 mg/kg bw to about 1.88 mg/kg bw, about 0.29 mg/kg bw to about 0.94 mg/kg bw, about 0.28 mg/kg bw to about 1.13 mg/kg bw or most preferably about 0.14 mg/kg bw to about 0.57 mg/kg bw.

In a further preferred embodiment, the suitable dose of liposomal paclitaxel is for application to a human patient is in an amount of about 0.01 to 2.5, preferably 0.02 to 1.88, and more preferably 0.25 to 1.88 mg/kg bw, particularly 1.54 mg/kg bw once a day and about 0.01 to 10, preferably 0.02 to 5.0 and more preferably 0.25 to 3.8 mg/kg bw, particularly 3.76 mg/kg bw per week.

For applications in human medicine, the present pharmaceutical composition may be administered at a monthly dose of preferably about 40 mg/m$^2$ up to about 3700 mg/m$^2$, particularly up to about 1022 mg/m$^2$ human body surface (bs), more preferably up to about 584 mg/m$^2$ bs, even more preferably up to about 480 mg/m$^2$ bs, and most preferably up to about 352 mg/m$^2$ bs.

In a preferred embodiment the present pharmaceutical composition is administered at a monthly dose of about 40 mg/m$^2$ bs up to about 584 mg/m$^2$ bs and more preferably of about 176 mg/m$^2$ bs up to about 352 mg/m$^2$ bs.

On an average, a human patient has a body surface of about 1.84 m$^2$. Thus, for an average person of 70 kg body weight and 172 cm height, preferred values for monthly doses, single doses etc. which have been indicated above in mg/kg body weight (bw) may be converted for human applications to corresponding values of in mg/m$^2$ human body surface (bs) by multiplication with a species-specific factor according to known methods.

The dose scheme can range from a plurality of times daily to a plurality of times during a month period, each of said times being separated by an interval of between days or weeks. The total treatment period is preferably at least one month.

The pharmaceutical composition is also suitable for a long-term administration for at least 3 months, for at least 4 months, for at least 6 months or for at least 12 months and up to 6 months, up to 12 months, up to 18 months, up to 24 months or even longer.

In a preferred embodiment the duration of the administration of the once or twice weekly dosing schedule is several weeks, preferably at least seven weeks.

Even in prolonged treatment schedules, the drug resistances or detrimental side-effects like alopecia, nephropathy are rarely observed. Further, usually no premedication like corticosteroids or anti-histamines is required.

The continued administration of lower doses once or twice weekly is at least as effective as the administration of a single high dose or frequent low dose administration interrupted by pause intervals. During the treatment interval the dose units and the dose intervals may remain constant. On the other hand, the dose units may be increased during the treatment interval, e.g. beginning with a starting dose and escalating in one or several steps to a consolidation dose, which may be 2, 3, 4 or even more times higher than the starting dose. Additionally or alternatively, the treatment interval between single doses may be altered, e.g. decreased or increased during the treatment period.

The term "about" as used in the present specification describes a deviation from the given value of up to plus or minus 5%.

The term "liposomal preparation" and "liposomes" are used synonymously throughout the present application. The liposomal preparation may be a component of a "pharmaceutical composition" and may be administered together with physiologically acceptable carriers such as a buffer.

The term "liposomal paclitaxel" or "lipid complexed paclitaxel" refers to a liposomal preparation comprising paclitaxel encapsulated within liposomes. A specific liposomal paclitaxel formulation is EndoTAG®-1. EndoTAG®-1, sometimes also referred to as MBT-0206, is a liposomal preparation with a molar ratio of 50:47:3 mole % of DOTAP, DOPC and paclitaxel. EndoTAG®-1 is a registered trademark in Germany.

The unit "mg/kg bw" refers to mg of liposomal paclitaxel per kg body weight. The unit "mg/m$^2$ bs" or just "mg/m$^2$" refers to mg liposomal paclitaxel per m$^2$ human body surface (bs). Thus, the dose calculation refers only to the mass of the paclitaxel portion, not the lipid portion.

The term "angiogenesis associated disease" or "angiogenic disease" refers to a disease which is dominated by the pathological growth of capillary blood vessels (Folkmann, J. and Klagsbrun, M. 1987, Angiogenic Factors. *Science* 235, 442-446). Examples of such a disease are e.g. diabetic retinopathy, chronic inflammatory diseases, rheumatoid arthritis, inflammation, dermatitis, psoriasis, stomach ulcers, tumor diseases such as hematogenous and solid tumors.

The term "chemosensitizer" refers to a substance or drug, which makes it easier for chemotherapy to affect, particularly kill cancer cells.

In a preferred embodiment, the cationic liposomal preparation of the present invention comprises at least one cationic lipid from about 30 mole % to about 99.9 mole %, preferably to about 98 mole % cationic lipid, paclitaxel in an amount of at least about 0.1 mole %, preferably of at least about 2 mole %; and at least one neutral and/or anionic lipid from about 0 mole % to about 70 mole % and is used for manufacturing a pharmaceutical composition for simultaneous, separate, or sequential combination therapy with a jointly effective dose of at least one further active agent and/or heat and/or radiation and/or cryotherapy.

In a further preferred embodiment, the liposomal preparation comprises paclitaxel in an amount of about 0.1 mole %, particularly of about 2 mole %, to about 8 mole %, preferably in an amount of about 0.5 mole %, particularly of about 2 mole %, to about 5 mole %, more preferably in an amount of about 1 mole % to about 4 mole % and most preferably in an amount of about 2.5 mole % to about 3.5 mole %. The cationic liposomal preparation of the present invention comprises substantially no paclitaxel crystals.

The liposomal preparation of the present invention is a cationic liposomal preparation which comprises cationic lipids in an amount of about 30 mole % to about 99.9 mole %, particularly to about 70 mole %, preferably from about 40 mole % to about 60 mole % and most preferably from about 45 mole %, to about 55 mole %. The liposomal preparation is characterized by having a positive zeta potential in about 0.05 M KCl solution at about pH 7.5 at room temperature.

The preferred cationic lipids of the liposomal preparation have a positive net charge and are N-[1-(2,3-dioleoyloxy)propyl]-N,N,N-trimethyl ammonium salts, e.g. the methylsulfate (DOTAP). Other useful lipids for the present invention may include:
DDAB, dimethyldioctadecyl ammonium bromide; 1,2-diacyloxy-3-trimethylammonium propanes, (including but not limited to: dioleoyl, dimyristoyl, dilauroyl, dipalmitoyl and distearoyl; also two different acyl chain can be linked to the glycerol backbone); N-[1-(2,3-dioloyloxy)propyl]-N,N-dimethyl amine (DODAP); 1,2-diacyloxy-3-dimethylammonium propanes, (including but not limited to: dioleoyl, dimyristoyl, dilauroyl, dipalmitoyl and distearoyl; also two different acyl chain can be linked to the glycerol backbone); N-[1-(2,3-dioleyloxy)propyl]-N,N,N-trimethylammonium chloride (DOTMA); 1,2-dialkyloxy-3-dimethylammonium propanes, (including but not limited to: dioleyl, dimyristyl, dilauryl, dipalmityl and distearyl; also two different alkyl chain can be linked to the glycerol backbone); dioctadecyla-midoglycylspermine (DOGS); 3β-[N—(N',N'-dimethylamino-ethane)carbamoyl]cholesterol (DC-Chol); 2,3-dioleoyloxy-N-(2-(sperminecarboxamido)-ethyl)-N,N-dimethyl-1-propanaminium trifluoro-acetate (DOSPA); β-alanyl cholesterol; cetyl trimethyl ammonium bromide (CTAB); diC14-amidine; N-tert-butyl-N'-tetradecyl-3-tetradecylamino-propionamidine; 14Dea2; N-(alpha-trimethylammonioacetyl)didodecyl-D-glutamate chloride (TMAG); O,O'-ditetradecanoyl-N-(trimethylammonio-acetyl)diethanolamine chloride; 1,3-dioleoyloxy-2-(6-carboxy-spermyl)-propylamide (DOSPER); N,N,N',N'-tetramethyl-N,N'-bis(2-hydroxylethyl)-2,3-dioleoyloxy-1,4-butanediammonium iodide; 1-[2-(acyloxy)ethyl]2-alkyl (alkenyl)-3-(2-hydroxyethyl)-imidazolinium chloride derivatives as described by Solodin et al. (1995) Biochem. 43:13537-13544, such as 1-[2-(9(Z)-octadecenoyloxy)ethyl]-2-(8(Z)-heptadecenyl-3-(2-hydroxyethyl) imidazolinium chloride (DOTIM), 1-[2-(hexadecanoyloxy)ethyl]-2-pentadecyl-3-(2-hydroxyethyl) imidazolinium chloride (DPTIM), 2,3-dialkyloxypropyl quaternary ammonium compound derivatives, containing a hydroxyalkyl moiety on the quaternary amine, as described e.g. by Feigner et al. [Feigner et al. *J. Biol. Chem.* 1994, 269, 2550-2561] such as: 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimethyl-hydroxypropyl ammonium bromide (DORIE-HP), 1,2-dioleyloxypropyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxyethyl ammonium bromide (DMRIE), 1,2-dipalmityloxypropyl-3-dimethyl-hydroxyethyl ammonium bromide (DPRIE), 1,2-disteryloxypropyl-3-dimethyl-hydroxyethyl ammonium bromide (DSRIE); cationic esters of acyl carnitines as reported by Santaniello et al. [U.S. Pat. No. 5,498,633]; cationic triesters of phospahtidylcholine, i.e. 1,2-diacyl-sn-glycerol-3-ethylphosphocholines, where the hydrocarbon chains can be saturated or unsaturated and branched or non-branched with a chain length from $C_{12}$ to $C_{24}$, the two acyl chains being not necessarily identical.

In a further preferred embodiment, the liposomal preparation optionally comprises at least one neutral and/or anionic lipid. Neutral lipids are lipids which have a neutral net charge. Anionic lipids or amphiphiles are molecules which have a negative net charge. These can be selected from sterols or lipids such as cholesterol, phospholipids, lysolipids, lysophospholipids, sphingolipids or pegylated lipids with a neutral or negative net change. Useful neutral and anionic lipids thereby include: phosphatidylserine, phosphatidylglycerol, phosphatidylinositol (not limited to a specific sugar), fatty acids, sterols, containing a carboxylic acid group for example, cholesterol, 1,2-diacyl-sn-glycero-3-phosphoethanolamine, including, but not limited to, DOPE, 1,2-diacyl-glycero-3-phosphocholines and sphingomyelin. The fatty acids linked to the glycerol backbone are not limited to a specific length or number of double bonds. Phospholipids may also have two different fatty acids. Preferably the further lipids are in the liquid crystalline state at room temperature and they are miscible (i.e. a uniform phase can be formed and no phase separation or domain formation occurs) with the used cationic lipid, in the ratio as they are applied. In a preferred embodiment the neutral lipid is DOPC.

In a further preferred embodiment, the liposomal preparation comprises optionally neutral and/or anionic lipids, preferably DOPC in an amount of about 30 mole % to about 70 mole %, preferably from about 40 mole % to about 60 mole % and more preferably from about 45 mole % to about 55 mole %.

It is a further object of the present invention that the cationic liposomal preparation which is used therein can be dehydrated, stored for extended periods of time while dehydrated, and then rehydrated when and where it is to be used, without losing a substantial portion of its contents during the dehydration, storage and rehydration processes. To achieve the latter, one or more protective agents, such as cryoprotectants, may be present. Thus, the inventive cationic liposome preparation preferably comprises a cryoprotectant, wherein the cryoprotectant is selected from a sugar or an alcohol or a combination thereof. Preferably, the cryoprotectant is selected from trehalose, maltose, sucrose, glucose, lactose, dextran, mannitol or sorbitol.

In a further preferred embodiment, the liposomal preparation comprises trehalose in the range of about 5% (m/v) to about 15% (m/v) with respect to the total volume of the preparation.

The formulation of the cationic liposomes of the present invention may vary. In a preferred embodiment the molar ratio is 50:47:3 mole % of DOTAP, DOPC and paclitaxel. This formulation is also designated MBT-0206 or EndoTAG-1.

Liposomes of various sizes are useful in the present invention. In a preferred embodiment of the present invention cationic liposomes have an average particle diameter from about 25 nm to about 500 nm, preferably from about 50 to about 500 nm, more preferably from about 100 nm to about 300 nm.

The present liposome compositions can be administered systemically, preferably intravenously. In a preferred embodiment, the liposomal composition is administered via intravenous infusion. The initial infusion rate may be about 0.5 ml/min. The rate may be stepwise, e.g. every 10 min, or continuously increased, until it reaches a maximum infusion rate of e.g. about 1.5 ml/min.

The cationic liposomes of the present invention may be used to treat any form of a condition associated with increased angiogenesis, such as cancer. The pharmaceutical composition of the present invention is particularly advantageous in treating tumors in human patients such as bladder cancer, breast cancer, colorectal cancer, endometrial cancer, leukaemia, lung cancer, lymphoma, melanoma, non-small-cell lung cancer, ovarian cancer, prostate cancer and to childhood cancers such as brain stem glioma, cerebellar astrocytoma, cerebral astrocytoma, ependymoma, Ewing's sarcoma/family of tumors, germ cell tumor, extracranial, Hodgkin's disease, leukaemia, acute lymphoblastic, leukaemia, acute myeloid, liver cancer, medulloblastoma, neuroblastoma, non-Hodgkin's lymphoma, osteosarcoma/malignant fibrous histiocytoma of bone, retinoblastoma, rhabdomyosarcoma, soft tissue sarcoma, supratentorial primitive neuroectodermal and pineal tumors, unusual childhood cancers, visual pathway and hypothalamic glioma, Wilms' Tumor and other childhood kidney tumors and to less common cancers including acute lymphocytic leukaemia, adult acute myeloid leukaemia, adult non-Hodgkin's lymphoma, brain tumor, cervical cancer, childhood cancers, childhood sarcoma, chronic lymphocytic leukaemia, chronic myeloid leukaemia, esophageal cancer, hairy cell leukaemia, kidney cancer, liver cancer, multiple myeloma, neuroblastoma, oral cancer, pancreatic cancer, primary central nervous system lymphoma, skin cancer, small-cell lung cancer, head & neck cancer, gall bladder and bile duct cancer, stomach cancer, gastrointestinal cancer, Kaposi's sarcoma, urothelial cell carcinoma, thyroid gland carcinoma, testicular carcinoma, vaginal cancer, angiosarcoma, soft tissue sarcoma, mesothelioma and hepatocellular carcinoma. Particularly, the cancer may be a mestastasing cancer and/or a standard (chemo)therapy-resistant cancer. Administration of the composition of the invention may slow or stop disease progression, or may lead to a partial or complete remission. Further conditions may be wound healing or an inflammatory disease or a chronic inflammatory disease such as rheumatoid arthritis, dermatitis, endometriosis or psoriasis.

The cationic liposomal preparations of the invention are particularly suitable for the treatment of cancer as indicated above, especially pancreatic cancer, inoperable pancreatic cancer, gastrointestinal cancer, cancer of the liver, lung cancer, colorectal or gastric cancer, breast cancer, prostate cancer and melanoma, either as a monotherapy or a combination therapy with further treatment therapies, e.g. further active agents as indicated below in detail, especially with chemotherapeutic agents, e.g. DNA/RNA antimetabolites such as gemcitabine.

Another preferred embodiment is the treatment of prostate cancer as monotherapy or in combination with at least one further active agent, particularly EndoTAG®-1 in combination with Prednisolon.

Generally, the cationic liposomal preparations of the invention may be administered as a first line treatment or as a second or third line treatment as a monotherapy, meaning the liposomal preparation comprising paclitaxel alone, or as a combination therapy, meaning the liposomal preparation comprising paclitaxel together with at least one further active agent such as gemcitabine.

The gold standard for the treatment of pancreatic cancer is gemcitabine (Gemzar®). The standard protocol according to the product information and publications such as Cantore. et al., 2004, J Chemother. 16(6): 589-94, and which is applied herein, is gemcitabine at a single dose of 1000 mg/m$^2$ bs applied over a time period of seven weeks once a week.

Thus, it is a preferred embodiment of the present invention to treat prostate cancer or pancreatic cancer or liver cancer in a monotherapy.

In an especially preferred embodiment cationic liposomal paclitaxel is administered as monotherapy using a twice weekly dosing schedule for a period of time of several weeks, preferably for at least seven weeks, for the treatment of cancer.

A twice weekly administration of lipid complexed paclitaxel (EndoTAG®-1) can be performed at different dose levels in patients with measurable locally advanced cancer such as pancreatic cancer, adenocarcinoma of the pancreas. Various single doses can be used for said treatment, preferably:

Cationic liposomal paclitaxel (EndoTAG®)-1) low dose: 11 mg/m$^2$ (=0.28 mg/kg body weight) lipid complexed paclitaxel Cationic liposomal paclitaxel (EndoTAG®)-1) medium dose: 22 mg/m$^2$ (=0.56 mg/kg body weight) lipid complexed paclitaxel Cationic liposomal paclitaxel (EndoTAG®-1) high dose: 44 mg/m$^2$ (=1.13 mg/kg body weight) lipid complexed paclitaxel Cationic liposomal paclitaxel (EndoTAG®-1) higher dose: 60 mg/m$^2$ (=1.54 mg/kg body weight) lipid complexed paclitaxel Patients therein receive infusions over a time period of at least seven weeks in twice weekly applications of EndoTAG®-1 (days 1, 4, 8, 11, 15, 18, 22, 25, 29, 32, 36, 39, 43, and 46). One complete cycle of this new regimen therefore comprises at least fourteen applications of EndoTAG®-1, which then consists of at least seven weeks.

In another preferred embodiment cationic liposomal paclitaxel is administered in combination therapy with a further active agent for the treatment of cancer.

In an especially preferred embodiment cationic liposomal paclitaxel is administered in combination with a further active agent for the treatment of pancreatic cancer, adenocarcinoma of the pancreas.

In another especially preferred embodiment, cationic liposomal paclitaxel is administered in combination with a further active agent for the treatment of prostate or liver cancer, particularly hepatocellular carcinoma.

In a most preferred embodiment cationic liposomal paclitaxel is administered in combination with gemcitabine for the treatment of pancreatic cancer using a twice weekly dosing schedule over a time frame of several weeks, preferably at least seven weeks.

In such a most preferred embodiment a 1st line combination treatment with weekly infusions of gemcitabine and twice weekly administration of liposomal paclitaxel (e.g. EndoTAG®-1) can be performed at various dose levels in patients with measurable locally advanced cancer such as pancreatic cancer, adenocarcinoma of the pancreas.

For the treatment of cancer such as pancreatic cancer, e.g. adenocarcinoma of the pancreas, using 1st line combination treatment with weekly infusions of gemcitabine and twice weekly administration of EndoTAG®-1, various single doses can be used, preferably:

Gemcitabine+EndoTAG®-1 (low dose: 11 mg/m$^2$ lipid complexed paclitaxel)

Gemcitabine+EndoTAG®-1 (medium dose: 22 mg/m$^2$ (=0.56 mg/kg body weight) lipid complexed paclitaxel Gemcitabine+EndoTAG®-1 (high dose: 44 mg/m$^2$ (=1.13 mg/kg body weight) lipid complexed paclitaxel)

Gemcitabine+EndoTAG®-1 (higher dose: 60 mg/m$^2$ (=1.54 mg/kg body weight) lipid complexed paclitaxel)

In a preferred embodiment patients receive a standardized chemotherapy regime, preferably gemcitabine, in combination with EndoTAG®-1 infusions over a time period of at least seven weeks. The treatment schedule preferably consists of a weekly gemcitabine treatment (days 4, 11, 18, 25, 32, 39, and 46) which is combined with a total of at least fourteen twice weekly applications of EndoTAG®-1 (days 1, 4, 8, 11, 15, 18, 22, 25, 29, 32, 36, 39, 43, and 46). One complete cycle of this new regimen therefore comprises at least seven applications of gemcitabine and at least fourteen applications of EndoTAG®-1, which then consists of at least seven weeks.

The further active agent for combination therapy is selected from a cytotoxic or cytostatic substance such as an anti-tumor or an anti-endothelial cell active substance, a chemotherapeutic agent or an immunological active substance, a compound that reduces or eliminates hypersensitivity reactions or a chemosensitizer. In a preferred embodiment, the liposomal composition is administered prior to the further active agent.

In a preferred embodiment, the active agent is selected from antineoplastic agents, especially antimitotic agents like paclitaxel, alkylating agents, especially platinum containing compounds like cisplatin, carboplatin, DNA topoisomerase inhibiting agents like camptothecin or doxorubicin, RNA/DNA antimetabolites, especially 5-fluorouracil or gemcitabine and/or other compounds having antitumor activity such as a statin, a depsipeptide, thalidomide, other agents interacting with microtubuli such as discodermolide, laulimalide, isolaulimalide, eleutherobin, Sarcodictyin A and B.

Especially preferred are combination therapies with cisplatin or carboplatin, with 5-fluorouracil or with gemcitabine.

In a further preferred embodiment, the compound that reduces or eliminates hypersensitivity reactions is selected from the group comprising (but not limited to) steroids, antihistamines, H2 receptor antagonists, and combinations thereof in a sufficient amount to prevent fatal anaphylactic reactions.

In an even more preferred embodiment the compound is selected from the group comprising Ranitidine, Dexamethasone, Diphenhydramine, Famotidine, Hydrocortisone, Clemastine, Cimetidine, Prednisolone, Prednison, Chlorpheniramine, Chlorphenamine, Dimethindene maleate, Indomethazine and Promethazine or any derivative thereof.

In a further preferred embodiment, the chemosensitizer is selected from the group comprising (but not limited to) cell cycle modulators, substances that revert a drug resistance like verapamil, vasoactive substances like anti-hypertensive drugs, substances that modify the charge-related interaction of cationic liposomes with blood components like protamine.

Preferably, the further active agent is present in a non-liposomal formulation.

In another aspect of the present invention said liposomal preparation comprises a taxane, preferably paclitaxel or docetaxel or a derivative thereof in an amount of about 0.1 to about 20 mol %, preferably in an amount of about 0.5 mole % to about 10 mole %, more preferably in an amount of about 1 mole % to about 5 mole % and most preferably in an amount of about 2 mole % to about 4 mole %.

It is another preferred embodiment of the invention that the cationic liposomal paclitaxel is administered in combination with a transarterial chemoembolization (TACE) therapy, percutaneous ethanol injection (PEI), radiofrequency thermal ablation (RFA) therapy, microwave thermal ablation and/or laser-induced thermotherapy (LITT) for the treatment of hepatocellular carcinomas. Transarterial chemoembolization can comprise the administration of gelfoam particles, gelatine sponges, starch, polyvinyl alcohol, ethanol, collagen, cytotoxic agents (e.g. mitomycin, doxorubicin, epirubicin, cisplatin) or iodized oil (Lididol). In a more preferred embodiment, cationic liposomal paclitaxel is administered e.g. once a week in combination with a transarterial chemoembolization (TACE).

It should be noted that all preferred embodiments discussed for one or several aspects of the invention also relate to all other aspects. This particularly refers to the amount and type of cationic lipid, the amount and type of neutral and/or anionic lipid, the amount and type of a taxane agent, the amount and type of a further active agent, particularly for combination therapy, and the type of disorder to be treated.

FIGURE LEGENDS

FIG. 1: Cationic liposomal paclitaxel (EndoTAG®-1) in twice weekly dosing schedule.

Schematic of the dose schedule for twice weekly application of liposomal paclitaxel. Cationic liposomal paclitaxel (EndoTAG®-1) is applied twice weekly (days 1, 4, 8, 11, 15, 18, 22, 25, 29, 32, 36, 39, 43, and 46) in three different doses: (low dose: 11 mg/m$^2$ lipid complexed paclitaxel); (medium dose: 22 mg/m$^2$ lipid complexed paclitaxel); (high dose: 44 mg/m$^2$ lipid complexed paclitaxel).

Figure 2:
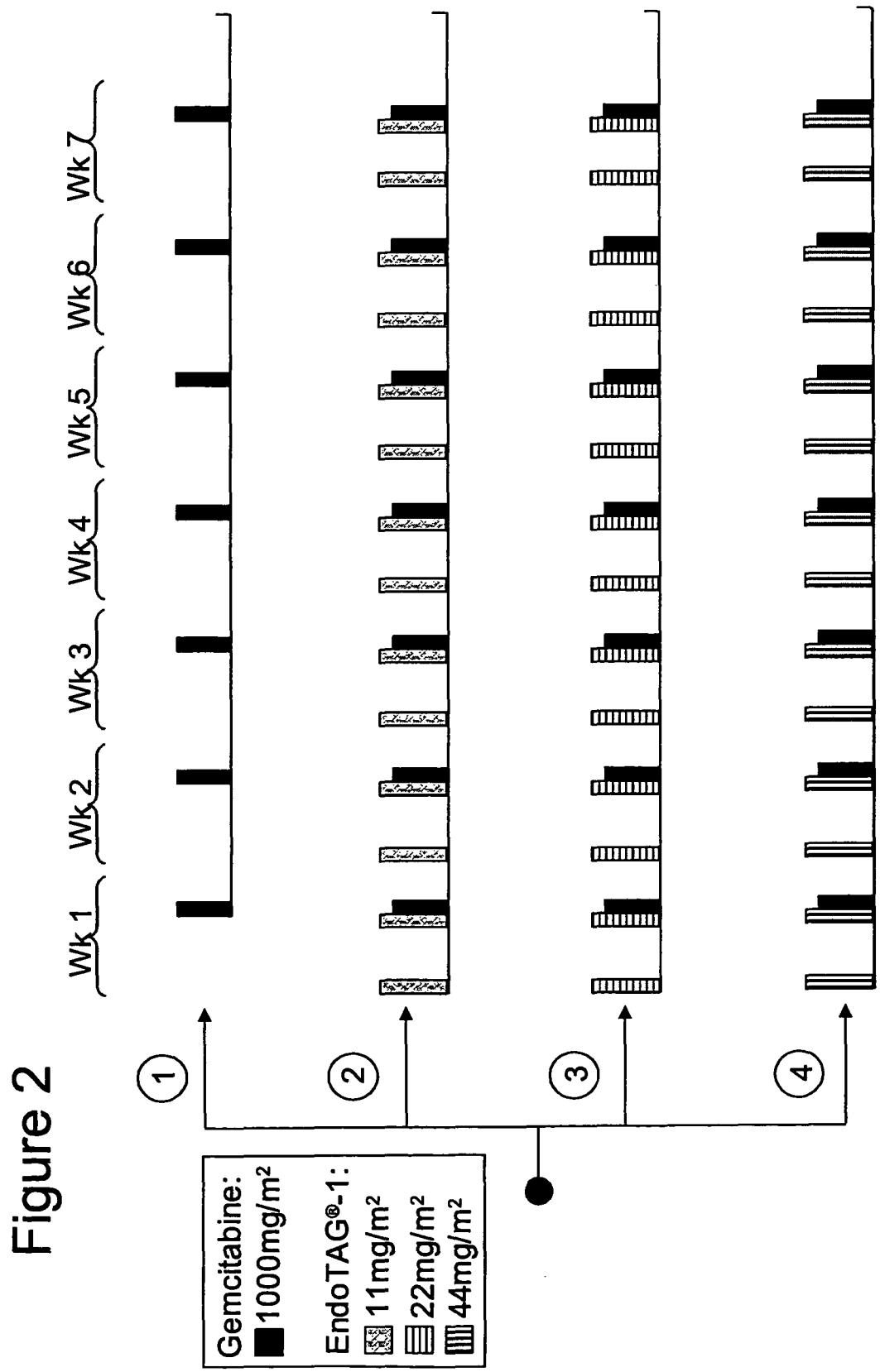

FIG. 2: Cationic liposomal paclitaxel (EndoTAG®-1) in a pancreatic cancer study.

Schematic of the dose schedule for twice weekly application of liposomal paclitaxel in combination with gemcitabine (Gemzar®) once weekly. The control group of patients receives 1: gemcitabine monotherapy. The other patients receive gemcitabine in combination with cationic liposomal paclitaxel (EndoTAG®-1) at three doses: 2: gemcitabine+ EndoTAG®-1 (low dose: 11 mg/m$^2$ lipid complexed paclitaxel); 3: gemcitabine+EndoTAG®-1 (medium dose: 22 mg/m$^2$ lipid complexed paclitaxel); 4: gemcitabine+EndoTAG®-1 (high dose: 44 mg/m$^2$ lipid complexed paclitaxel).

Gemcitabine is applied at a dose of 1000 mg/m$^2$ body surface once a week (Mon; =days 4, 11, 18, 25, 32, 39, and 46). Cationic liposomal paclitaxel (EndoTAG®-1) is applied twice weekly (days 1, 4, 8, 11, 15, 18, 22, 25, 29, 32, 36, 39, 43, and 46).

The following examples should be illustrative only but are not meant to be limiting to the scope of the invention. Other generic and specific configurations will be apparent to those skilled in the art.

EXAMPLES

Example 1

Human Therapy Treatment Protocol

This example is concerned with human treatment protocols using the formulations disclosed. Treatment will be of use preventing and/or treating various human diseases and disorders associated with enhanced angiogenic activity. It is considered to be particularly useful in anti-tumor therapy, for example, in treating patients with solid tumors and hematological malignancies or in therapy against a variety of chronic inflammatory diseases such as rheumatoid arthritis or psoriasis.

A feature of the invention is that several classes of diseases and/or abnormalities may be treated by directly targeting angiogenic epithelial cells without directly targeting the tissue or cells involved in the abnormality, e.g. by inhibiting angiogenesis the blood supply to a tumor is cut off and the tumor is killed without directly targeting the tumor cells in any manner. Other classes of diseases and/or abnormalities may be treated by directly targeting angiogenic endothelial cells and by directly targeting the tissue or cells involved in the abnormality.

In another application, drug resistant cells such as drug resistant cancer cells or highly proliferative synoviocytes in rheumatoid arthritis can be affected directly.

The various elements of conducting a clinical trial, including patient treatment and monitoring, will be known to those skilled in the art in light of the present disclosure.

For regulatory approval purposes, it is contemplated that patients chosen for a study are either anti-neoplastic treatment naive or would have failed to respond to at least one course of conventional therapy and would have objectively measurable disease as determined by physical examination, laboratory techniques, or radiographic procedures. Such patients would also have no history of clinically relevant cardiac or renal disease and any chemotherapy should be stopped at least 2 weeks before entry into the study.

Prior to application, the formulation can be reconstituted in an aqueous solution in the event that the formulation was freeze dried. As outlined above, the required application volume is calculated from the patient's body weight and the dose schedule.

The disclosed formulations may be administered over a short to medium infusion time. The infusion given at any dose level should be dependent upon the toxicity achieved after each. Thus, if Grade II toxicity was reached after any single infusion, or at a particular period of time for a steady rate infusion, further doses should be withheld or the steady rate infusion stopped unless toxicity improved. Increasing doses should be administered to groups of patients until approximately 60% of patients showed unacceptable Grade III or IV toxicity in any category. Doses that are ⅔ of this value would be defined as the safe dose.

Physical examination, tumor measurements and laboratory tests should, of course, be performed before treatment and at intervals of about 3-4 weeks later. Laboratory tests should include complete blood cell counts, serum creatinine, creatine kinase, electrolytes, urea, nitrogen, SGOT, bilirubin, albumin and total serum protein.

Clinical responses may be defined by acceptable measure or changes in laboratory values e.g. tumor markers. For example, a complete response may be defined by the disappearance of all measurable disease for at least a month, whereas a partial response may be defined by a 50% or greater reduction.

All of the compositions and methods disclosed and claimed herein can be made and executed without undue experimentation in light of the present disclosure. While the compositions and methods of this invention have been described in terms of preferred embodiments, it will be apparent to those skilled in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by the FDA Office of Biologics standards.

The present invention includes a method of delivery of a pharmaceutically effective amount of the inventive formulation of an active agent to a target site such as an angiogenic vascular target site of a subject in need thereof. A "subject in need thereof" refers to a mammal, e.g. a human.

The route of administration preferably comprises peritoneal or parenteral administration.

For use with the present invention the "pharmacologically effective amount" of a compound administered to a subject in need thereof will vary depending on a wide range of factors. The amount of the compound will depend upon the size, age, sex, weight, and condition of the patient, as well as the potency of the substance being administered. Having indicated that there is considerable variability in terms of dosing, it is believed that those skilled in the art can, using the present disclosure, readily determine appropriate dosing by first administering extremely small amounts and incrementally increasing the dose until the desired results are obtained. Although the amount of the dose will vary greatly based on factors as described above, in general, the present invention makes it possible to administer substantially smaller amounts of any substance as compared with delivery systems which only target the pathologic tissue, e.g. target the tumor cells themselves.

Example 2

Twice Weekly Administration Protocol for Cationic Liposomal Paclitaxel (FIG. 1)

Indication: Pancreatic Cancer; adenocarcinoma of the pancreas

Study Design:

A controlled, -three armed, randomized, open label clinical phase II trial 1st line treatment with twice weekly administration of lipid complexed paclitaxel (EndoTAG®-1) in three dose levels compared with gemcitabine monotherapy in patients with measurable locally advanced and/or metastatic adenocarcinoma of the pancreas is performed.

The four treatment arms consist of (see FIG. 1):
Arm 1: Gemcitabine monotherapy (control group): 1000 mg/m$^2$ (=25.67 mg/kg body weight)
Arm 2: EndoTAG®-1 (low dose: 11 mg/m$^2$ (=0.28 mg/kg body weight) lipid complexed paclitaxel)
Arm 3: EndoTAG®-1 (medium dose: 22 mg/m$^2$ (=0.56 mg/kg body weight) lipid complexed paclitaxel)
Arm 4: EndoTAG®-1 (high dose: 44 mg/m$^2$ (=1.13 mg/kg body weight) lipid complexed paclitaxel)

Patients with advanced and/or metastatic adenocarcinoma of the pancreas that are considered unresectable are eligible to enter the study after signing informed consent and having undergone baseline evaluation. Those patients meeting study eligibility criteria will either receive a standardized chemotherapy regime (i.e. gemcitabine) as a monotherapy or EndoTAG®-1 infusions. Seven weekly applications of gemcitabine will be administered in arm 1 (gemcitabine monotherapy control arm without EndoTAG®-1). In arms 2, 3 and 4 seven weeks of fourteen twice weekly applications of EndoTAG®-1 (days 1, 4, 8, 11, 15, 18, 22, 25, 29, 32, 36, 39, 43, and 46) are performed. In summary, one complete cycle of this new regimen comprises fourteen applications of EndoTAG®-1, which then consists of seven weeks (arms 2, 3, and 4).

Example 3

Combination Therapy of Cationic Liposomal Paclitaxel (EndoTAG®-1) Twice Weekly in Combination with Gemcitabine Once Weekly (FIG. 2)

Study No. Indication

CT4001 Pancreatic Cancer; adenocarcinoma of the pancreas

Study Design CT 4001:

A controlled, -four armed, randomized, open label clinical phase II trial 1st line combination treatment with weekly infusions of gemcitabine and twice weekly administration of lipid complexed paclitaxel (EndoTAG®-1) in three single dose levels compared with gemcitabine monotherapy in patients with measurable locally advanced and/or metastatic adenocarcinoma of the pancreas is performed.

The four treatment arms consist of (see FIG. 2):
Arm 1: Gemcitabine monotherapy (control group): 1000 mg/m$^2$ (=25.67 mg/kg body weight)
Arm 2: Gemcitabine+EndoTAG®-1 (low dose: 11 mg/m$^2$ (=0.28 mg/kg body weight) lipid complexed paclitaxel)

Arm 3: Gemcitabine+EndoTAG®-1 (medium dose: 22 mg/m² (=0.56 mg/kg body weight) lipid complexed paclitaxel)

Arm 4: Gemcitabine+EndoTAG®-1 (high dose: 44 mg/m² (=1.13 mg/kg body weight) lipid complexed paclitaxel)

Patients with advanced and/or metastatic adenocarcinoma of the pancreas that are considered unresectable are eligible to enter the study after signing informed consent and having undergone baseline evaluation. Those patients meeting study eligibility criteria will either receive a standardized chemotherapy regime (i.e. gemcitabine) as a monotherapy or gemcitabine preceded by EndoTAG®-1 infusions. Seven weekly applications of gemcitabine will be administered in arm 1 (gemcitabine monotherapy control arm without EndoTAG®-1). In arms 2, 3, and 4 seven weeks of gemcitabine treatment (days 4, 11, 18, 25, 32, 39, and 46) will be combined with a total of fourteen twice weekly applications of EndoTAG®-1 (days 1, 4, 8, 11, 15, 18, 22, 25, 29, 32, 36, 39, 43, and 46). In summary, one complete cycle of this new regimen comprises seven applications of gemcitabine (all arms) and fourteen applications of EndoTAG®-1, which then consists of seven weeks (arms 2, 3, and 4).

Conclusion

Treatments with high doses of EndoTAG®-1 can be replaced by using low doses at a higher frequency. There is a correlation between treatment density (no. of treatments per week) and treatment efficacy. The optimised dosing regimen potentially reduces toxic side effects caused by high dose treatments and reduces physical burden of the patient, which leads to an improved quality of life.

Example 4

Treatment of Liver Cancer (Hepatocellular Carcinoma)

Study Design:

A controlled, two-armed, randomized, open label clinical phase II trial, comparing TACE therapy only to TACE (transarterial chemoembolization) therapy combined with once weekly administration of lipid complexed paclitaxel (EndoTAG®-1) is performed.

The two treatment arms consist of:
Arm 1: TACE therapy alone (control group);
Arm 2: TACE therapy in combination with once weekly EndoTAG®-1 (44 mg/m² lipid complexed paclitaxel).

Patients with irresectable histological/cytological proven hepatocellular carcinoma (HCC) who have shown responsiveness to TACE therapy are eligible to enter the study after signing informed consent and having undergone baseline evaluation. Those patients meeting study eligibility criteria are randomized and either receive TACE therapy or TACE therapy in combination with a once a week administration of 44 mg/m² EndoTAG®-1, an interim analysis determining progression or response based on DCE-MRI and MRI scans is performed. Progression-free-survival (PFS) is determined is as the primary efficacy parameter in the study.

REFERENCE LIST

1. Rowinsky, E. K., and R. C. Donehower. 1995. paclitaxel (paclitaxel). *N Engl J Med* 332:1004-1014.
2. Awada, A. 2002. New cytotoxic agents and molecular-targeted therapies in the treatment of metastatic breast cancer. *Forum (Genova)* 12:4-15.
3. Seidman, A. D. 2003. Monotherapy options in the management of metastatic breast cancer. *Semin Oncol* 30:6-10.
4. Romanini, A., L. Tanganelli, F. Camino, A. Fanucchi, R. Lionetto, S. Pastorino, S. Cosio, A. Gadducci, and P. F. Conte. 2003. First-line chemotherapy with epidoxorubicin, paclitaxel, and carboplatin for the treatment of advanced epithelial ovarian cancer patients. *Gynecol Oncol* 89:354-359.
5. Blom, R., N. Palm, and E. Simonsen. 1996. paclitaxel (paclitaxel) monotherapy in the treatment of progressive and recurrent ovarian carcinoma after platinum-based chemotherapy. *Acta Oncol* 35:733-736.
6. Modi, S., K. S. Panageas, E. T. Duck, A. Bach, N. Weinstock, J. Dougherty, L. Cramer, C. Hudis, L. Norton, and A. Seidman. 2002. Prospective exploratory analysis of the association between tumor response, quality of life, and expenditures among patients receiving paclitaxel monotherapy for refractory metastatic breast cancer. *J Clin Oncol* 20:3665-3673.
7. Ozols, R. F., B. N. Bundy, B. E. Greer, J. M. Fowler, D. Clarke-Pearson, R. A. Burger, R. S. Mannel, K. DeGeest, E. M. Hartenbach, and R. Baergen. 2003. Phase III trial of carboplatin and paclitaxel compared with cisplatin and paclitaxel in patients with optimally resected stage III ovarian cancer: a Gynecologic Oncology Group study. *J Clin Oncol* 21:3194-3200.
8. Vogelstein, B., E. R. Fearon, S. R. Hamilton, S. E. Kern, A. C. Preisinger, M. Leppert, Y. Nakamura, R. White, A. M. Smits, and J. L. Bos. 1988. Genetic alterations during colorectal-tumor development. *N Engl J Med* 319:525-532.
9. Kerbel, R. S. 1991. Inhibition of tumor angiogenesis as a strategy to circumvent acquired resistance to anti-cancer therapeutic agents. *Bioessays* 13:31-36.
10. Schünemann, Possinger, Scheidel, and Willich. 1999. Gynäkologische Malignome. Zuckschwerdt GmbH, Germering/München.
11. Heidemann, E., B. Steinke, and H. D. Waller. 1997. Therapieschemata Onkologie und Hämatologie. Urban & Schwarzenberg, München.
12. Heinemann, V. 2003. Role of gemcitabine in the treatment of advanced and metastatic breast cancer. *Oncology* 64:191-206.
13. Thigpen, J. T., J. A. Blessing, G. Olt, S. S. Lentz, and J. Bell. 2003. Cisplatin as second-line therapy in ovarian carcinoma treated initially with single-agent paclitaxel: a Gynecologic Oncology Group study. *Gynecol Oncol* 90:581-586.
14. Kuenen, B. C., L. Rosen, E. F. Smit, M. R. Parson, M. Levi, R. Ruijter, H. Huisman, M. A. Kedde, P. Noordhuis, W. J. van der Vijgh, G. J. Peters, G. F. Cropp, P. Scigalla, K. Hoekman, H. M. Pinedo, and G. Giaccone. 2002. Dose-finding and pharmacokinetic study of cisplatin, gemcitabine, and SU5416 in patients with solid tumors. *J Clin Oncol* 20:1657-1667.
15. Sledge, G. W., Jr. 2003. Gemcitabine combined with paclitaxel or paclitaxel/trastuzumab in metastatic breast cancer. *Semin Oncol* 30:19-21.
16. Reck, M., J. von Pawel, H. N. Macha, E. Kaukel, K. M. Deppermann, R. Bonnet, K. Ulm, S. Hessler, and U. Gatzemeier. 2003. Randomized phase III trial of paclitaxel, etoposide, and carboplatin versus carboplatin, etoposide, and vincristine in patients with small-cell lung cancer. *J Natl Cancer Inst* 95:1118-1127.
17. Zimpfer-Rechner, C., U. Hofmann, R. Figl, J. C. Becker, U. Trefzer, I. Keller, A. Hauschild, and D. Schadendorf. 2003. Randomized phase II study of weekly paclitaxel versus paclitaxel and carboplatin as second-line therapy in disseminated melanoma: a multicentre trial of the Dermatologic Co-operative Oncology Group (DeCOG). *Melanoma Res* 13:531-536.
18. Sledge, G. W., D. Neuberg, P. Bernardo, J. N. Ingle, S. Martino, E. K. Rowinsky, and W. C. Wood. 2003. Phase III trial of doxorubicin, paclitaxel, and the combination of doxorubicin and paclitaxel as front-line chemotherapy for metastatic breast cancer: an intergroup trial (E1193). *J Clin Oncol* 21:588-592.
19. Nobmann, S., B. Bauer, and G. Fricker. 2001. Ivermectin excretion by isolated functionally intact brain endothelial capillaries. *Br J Pharmacol* 132:722-728.
20. Thomas, H., and H. M. Coley. 2003. Overcoming multidrug resistance in cancer: an update on the clinical strategy of inhibiting p-glycoprotein. *Cancer Control* 10:159-165.
21. Harker, W. G., and B. I. Sikic. 1985. Multidrug (pleiotropic) resistance in doxorubicin-selected variants of the human sarcoma cell line MES-SA. *Cancer Res* 45:4091-4096.
22. Fellner, S., B. Bauer, D. S. Miller, M. Schaffrik, M. Fankhanel, T. Spruss, G. Bernhardt, C. Graeff, L. Farber, H. Gschaidmeier, A. Buschauer, and G. Fricker. 2002. Transport of paclitaxel (paclitaxel) across the blood-brain barrier in vitro and in vivo. *J Clin Invest* 110:1309-1318.
23. Kiesewetter, D. O., E. M. Jagoda, C. H. Kao, Y. Ma, L. Ravasi, K. Shimoji, L. P. Szajek, and W. C. Eckelman. 2003. Fluoro-, bromo-, and iodo paclitaxel derivatives: synthesis and biological evaluation. *Nucl Med Biol* 30:11-24.
24. Kohler, S., and W. D. Stein. 2003. Optimizing chemotherapy by measuring reversal of P-glycoprotein activity in plasma membrane vesicles. *Biotechnol Bioeng* 81:507-517.
25. Leonard, G. D., O. Polgar, and S. E. Bates. 2002. ABC transporters and inhibitors: new targets, new agents. *Curr Opin Investig Drugs* 3:1652-1659.
26. Agrawal, M., J. Abraham, F. M. Balis, M. Edgerly, W. D. Stein, S. Bates, T. Fojo, and C. C. Chen. 2003. Increased 99 mTc-sestamibi accumulation in normal liver and drug-resistant tumors after the administration of the glycoprotein inhibitor, XR9576. *Clin Cancer Res* 9:650-656.
27. Callies, S., D. P. de Alwis, A. Harris, P. Vasey, J. H. Beijnen, J. H. Schellens, M. Burgess, and L. Aarons. 2003. A population pharmacokinetic model for paclitaxel in the presence of a novel P-gp modulator, Zosuquidar Trihydrochloride (LY335979). *Br J Clin Pharmacol* 56:46-56.
28. Lindl, T., and J. Bauer. 1994. Zell-und Gewebekultur. Gustav Fischer Verlag, Stuttgart.
29. Harker, W. G., D. Bauer, B. B. Etiz, R. A. Newman, and B. I. Sikic. 1986. Verapamil-mediated sensitization of doxorubicin-selected pleiotropic resistance in human sarcoma cells: selectivity for drugs which produce DNA scission. *Cancer Res* 46:2369-2373.
30. Folkmann, J. and Klagsbrun M. 1987, Angiogenic Factors. *Science* 235, 442-446.
31. Cantore. et al., 2004, Gemcitabine versus FLEC regimen given intra-arterially to patients with unresectable pancreatic cancer: a prospective, randomized phase III trial of the Italian Society of Integrated Locoregional Therapy in Oncology. *J Chemother.* 16(6): 589-94.

The invention claimed is:

1. A method of treating pancreatic cancer comprising administering to a human subject in need thereof a cationic liposomal formulation comprising at least one cationic lipid in an amount from about 30 mole % to about 99.9 mole %, paclitaxel in an amount of at least about 0.1 mole %, and a neutral lipid in an amount from about 30 mole % to about 70 mole %, wherein the cationic liposomaal formulation has a positive zeta potential in about 0.05 M KCl solution at about pH 7.5 at room temperature, and wherein the liposomal formulation is administered twice a week, wherein a single dose of paclitaxel is about 0.05 mg/kg body weight (bw) to about 1.25 mg/kg bw of the patient.

2. The method of claim 1, wherein the formulation is for simultaneous, separate, or sequential combination therapy with a jointly effective dose of at least one further active agent, or with heat, or with radiation, or with cryotherapy.

3. The method of claim 2, wherein the further active agent is a chemotherapeutic agent.

4. The method of claim 2, wherein the further active agent is selected from the group consisting of an alkylating agent, DNA topoisomerase inhibiting agent, RNA/DNA antimetabolite, and prednisolone.

5. The method of claim 3, wherein the chemotherapeutic agent is selected from the group consisting of an anti-tumor active agent, an immunological active agent, and a chemosensitizer.

6. The method of claim 5, wherein the antitumor active agent is an anti-endothelial cell active agent.

7. The method of claim 5, wherein the immunological active agent is a compound that reduces or eliminates hypersensitivity reactions.

8. The method of claim 1, wherein the cationic lipid is selected from the group consisting of N-[1-(2,3-dioleoyloxy)propyl]-N,N,N-trimethyl ammonium salt (DOTAP); dimethyldioctadecyl ammonium bromide (DDAB); 1,2-diacyloxy-3-trimethylammonium propane N-[1-(2,3-dioloyloxy)propyl]-N, N-dimethyl amine (DODAP); 1,2-diacyloxy-3-dimethylammonium propane; N-[1-(2,3-dioleyloxy)propyl]-N,N,N-trimethylammonium chloride (DOTMA); 1,2-dialkyloxy-3-dimethylammonium propane; dioctadecylamidoglycylspermine (DOGS); 3β[N-(N',N'-dimethylamino-ethane) carbamoyl]cholesterol (DC-Chol); 2, 3-dioleoyloxy-N-(2(sperminecarboxamido)-ethyl) -N,N-dimethyl-1-propanaminium trifluoroacetate (DOSPA); β3-alanyl cholesterol; cetyl trimethyl ammonium bromide (CTAB); diC14-amidine; N-tert-butyl-N'-tetradecyl-3-tetradecylamino-propionamidine; 14Dea2; N-(alpha-trimethylammonioacetyl)didodecyl-D-glutamate chloride (TMAG); O,O'-ditetradecanoyl-N-(trimethylammonioacetyl)diethanolamine chloride; 1,3-dioleoyloxy-2-(6-carboxy-spermyl)-propylamide (DOSPER); N,N,N,N,'-tetramethyl-N,N'-bis(2-hydroxylethyl)-2,3-dioleoyloxy-1,4-butanediammonium iodide; 1[2-(acyloxy)ethyl]2-alkyl (alkenyl)-3-(2-hydroxyethyl)imidazolinium chloride: 1,2-dioleoyl-3-dimeythyl-hydroxyethylammonium bromide (DORI); 1,2-dioleyloxypropyl-3-dimethylhydroxyethylammonium bromide (DORIE); 1,2-dioleyloxypropyl-3-dimethylhydroxybutylammonium bromide (DORIE-HP); 1,2-dioleyloxypropyl-3-dimethylhydroxybutylammonium bromide (DORIE-HS); 1,2-dioleyloxypropyl-3-dimethylhydroxypentylammonium bromide (DORIE-Hpe); 1,2-dimyristyloxypropyl-3-dimethylhydroxylethylammonium bromide (DMRIE); 1,2-dipalmityloxypropyl-3-dimethylhydroxyethylammonium bromide (DPRIE); 1,2-disteryloxypropyl-3-dimethylhydroxyethylammonium bromide (DSR1E); and 1,2-diacyl-sn-glycerol-3-ethylphosphocholine.

9. The method of claim 7, wherein the compound that reduces or eliminates hypersensitivity reactions is selected from the group consisting of steroids, antihistamines, H2 receptor antagonists, and combinations thereof in a sufficient amount to prevent fatal anaphylactic reactions.

10. The method of claim 7, wherein the compound that reduces or eliminates hypersensitivity reactions is selected from the group consisting of Ranitidine, Dexamethasone, Diphenhydramine, Famotidine, Hydrocortisone, Clemastine, Cimetidine, Prednisolone, Chlorpheniramine, Chlorphenamine, Dimethindene maleate, and Promethazine.

11. The method of claim 5, wherein the chemosensitizer is selected from the group consisting of cell cycle modulators, substances that revert drug resistance, and vasoactive substances.

12. The method of claim 1, wherein the cationic liposomal formulation comprises paclitaxel in an amount of at least about 2 mole % to about 8 mole %.

13. The method of claim 1, wherein the cationic liposomal formulation comprises paclitaxel in an amount of at least about 2.5 mole % to about 3.5 mole %.

14. The method of claim 1, wherein the cationic liposomal formulation comprises 50:47:3 mole % of DOTAP, DOPC, and paclitaxel.

15. The method of claim 1, wherein the cationic liposomal formulation comprises substantially no paclitaxel crystals.

16. The method of claim 1, wherein the cationic liposomal formulation comprises liposomes having an average particle diameter from about 25 nm to about 500 nm, or about 100 nm to about 300 nm.

17. The method of claim 1, wherein the cationic liposomal formulation is administered systemically or intravenously.

18. The method of claim 1, wherein the cationic liposomal formulation is a component of a pharmaceutical composition and is administered together with at least one physiologically acceptable carrier such as a buffer.

19. The method of claim 2, wherein the further active agent is gemcitabine.

20. The method of claim 1, wherein the method further comprises at least a further active agent for treating pancreatic cancer.

21. The method of claim 1, in combination with a transarterial chemoembolization therapy for treating pancreatic cancer.

22. The method of claim 8, wherein the 1-[2(acyloxy)ethyl]2-alkyl (alkenyl)-3-(2-hydroxyethyl)-imidazolinium chloride is 1-[2-(9(Z)-octadecenoyloxy)ethyl]-2-(8(Z)-heptadecenyl-3-(2-hydroxyethyl)-imidazoliniumchloride (DOTIM) or 1-[2-(hexadecanoyloxy)ethyl]-2-pentadecyl-3-(2-hydroxyethyl)imidazolinium chloride (DPTIM).

23. The method of claim 1, wherein the neutral lipid is selected from the group consisting of cholesterol, phospholipid, lysolipid, sphingolipid, and pegylated lipid with a neutral charge.

24. The method of claim 1, wherein the neutral lipid is selected from the group consisting of 1,2-diacyl-sn-glycero-3-phosphoethanolamine, 1,2-diacyl-sn-glycero-3-phosphocholine, and sphingomyelin.

25. The method of claim 24 wherein 1,2-diacyl-sn-glycero-3-phosphoethanolamine is 1,2-dioleoyl-sn-glycero-3-phosphoethanolamine (DOPE).

26. The method of claim 24, wherein 1,2-diacyl-sn-glycero-3-phosphocholine is 1,2-dioleoyl-sn-glycero-3-phosphocholine (DOPC).

27. The method of claim 1, wherein the liposomal formulation comprises DOTAP, DOPC, and paclitaxel.

28. The method of claim 1, wherein the liposomal formulation further comprises an anionic lipid in an amount of 30 mole % to 55 mole %.

29. The method of claim 23, wherein the neutral lipid is lysophospholipid.

* * * * *